(12) United States Patent
Wenzel et al.

(10) Patent No.: US 10,331,981 B2
(45) Date of Patent: Jun. 25, 2019

(54) BRAIN TISSUE CLASSIFICATION

(71) Applicant: KONINKLIJKE PHILIPS N.V., Eindhoven (NL)

(72) Inventors: Fabian Wenzel, Hamburg (DE); Thomas Heiko Stehle, Hamburg (DE); Lyubomir Georgiev Zagorchev, Burlington, MA (US); Jochen Peters, Norderstedt (DE); Martin Bergtholdt, Hamburg (DE); Carsten Meyer, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 3 days.

(21) Appl. No.: 15/564,263

(22) PCT Filed: Apr. 25, 2016

(86) PCT No.: PCT/EP2016/059115
§ 371 (c)(1),
(2) Date: Oct. 4, 2017

(87) PCT Pub. No.: WO2016/173957
PCT Pub. Date: Nov. 3, 2016

(65) Prior Publication Data
US 2018/0137394 A1 May 17, 2018

Related U.S. Application Data

(60) Provisional application No. 62/154,768, filed on Apr. 30, 2015.

(30) Foreign Application Priority Data

Jun. 2, 2015 (EP) .................................... 15170208

(51) Int. Cl.
G06K 9/62 (2006.01)
G06K 9/20 (2006.01)
(Continued)

(52) U.S. Cl.
CPC .......... *G06K 9/6277* (2013.01); *A61B 5/0042* (2013.01); *A61B 5/055* (2013.01);
(Continued)

(58) Field of Classification Search
CPC . G06T 7/11; G06T 7/143; G06T 2207/20076; G06T 2207/30016;
(Continued)

(56) References Cited

U.S. PATENT DOCUMENTS 8,213,696 B2   7/2012 Lakare
8,564,593 B2   10/2013 Johnson et al.
(Continued)

OTHER PUBLICATIONS

Harmouche, R., "Probabilistic Multiple Sclerosis Lesion Classification Based on Modeling Regional Intensity Variability and Local Neighborhood Information", IEEE Transactions on Biomedical Engineering, IEEE Service Center, Piscataway, NJ, vol. 62, No. 5, Apr. 17, 2015, pp. 1281-1292.
(Continued)

*Primary Examiner* — Kenny A Cese

(57) ABSTRACT

A system and method are provided for brain tissue classification, which involves applying an automated tissue classification technique to an image of a brain based on a prior probability map, thereby obtaining a tissue classification map of the brain. A user is enabled to, using a user interaction subsystem, provide user feedback which is indicative of a) an area of misclassification in the tissue classification map and b) a correction of the misclassification. The prior probability map is then adjusted based on the user feedback to obtain an adjusted prior probability map,
(Continued)

and the automated tissue classification technique is re-applied to the image based on the adjusted prior probability map. An advantage over a direct correction of the tissue classification map may be that the user does not need to indicate the area of misclassification or the correction of the misclassification with a highest degree of accuracy. Rather, it may suffice to provide an approximate indication thereof.

13 Claims, 4 Drawing Sheets

(51) Int. Cl.
    *G06T 7/00*        (2017.01)
    *A61B 5/00*        (2006.01)
    *A61B 5/055*      (2006.01)

(52) U.S. Cl.
    CPC .......... *G06K 9/2081* (2013.01); *G06T 7/0012* (2013.01); *A61B 2576/026* (2013.01); *G06T 2200/24* (2013.01); *G06T 2207/20076* (2013.01); *G06T 2207/20092* (2013.01); *G06T 2207/20128* (2013.01); *G06T 2207/30016* (2013.01)

(58) Field of Classification Search
    CPC ......... G06T 7/0012; G06T 2207/20128; G06T 2207/30096; G06T 7/12; G06T 2207/20192; G06K 9/00234
    See application file for complete search history.

(56) References Cited

U.S. PATENT DOCUMENTS

| | | | |
|---|---|---|---|
| 8,577,115 B2 | 11/2013 | Gering et al. | |
| 8,831,328 B2 | 9/2014 | Gupta et al. | |
| 2002/0186882 A1* | 12/2002 | Cotman | G06K 9/00127 |
| | | | 382/165 |
| 2009/0226060 A1* | 9/2009 | Gering | G06T 7/11 |
| | | | 382/128 |
| 2012/0093381 A1 | 4/2012 | Fan et al. | |
| 2012/0320055 A1* | 12/2012 | Pekar | G06T 7/0012 |
| | | | 345/424 |
| 2013/0243287 A1 | 9/2013 | Thomson et al. | |
| 2015/0036900 A1 | 2/2015 | Vik et al. | |
| 2015/0045651 A1* | 2/2015 | Crainiceanu | A61B 5/055 |
| | | | 600/410 |

OTHER PUBLICATIONS

Van Leemput, K., "Probabilistic Brain Atlas Encoding Using Bayesian Inference", Oct. 2006, Medical Image Computing and Computer-Assisted Intervention—MICCAI 2006 Lecture Notes in Computer Science; LNCS, Springer, Berlin, pp. 704-711.

\* cited by examiner

BRAIN TISSUE CLASSIFICATION

CROSS-REFERENCE TO PRIOR APPLICATIONS

This application is the U.S. National Phase application under 35 U.S.C. § 371 of International Application No. PCT/EP2016/059115, filed on Apr. 25, 2016, which claims the benefit of U.S. Patent Application No. 62/154,768 filed on Apr. 30, 2015 and European Patent Application No. 15170208.1, filed on Jun. 2, 2015. These applications are hereby incorporated by reference herein.

FIELD OF THE INVENTION

The invention relates to a system and a method for brain tissue classification. The invention further relates to a workstation and imaging apparatus comprising the system. The invention further relates to a computer program product comprising instructions for causing a processor system to perform the method.

BACKGROUND OF THE INVENTION

The role of imaging in the detection and differential diagnosis of neuro-degenerative diseases has increased in recent years. One reason is the emerging availability of quantification techniques that are able to detect subtle changes in the brain which occur in an early phase of the disease, or even in a pre-symptomatic phase. For example, T1-weighted Magnetic Resonance Imaging (MRI) scans are widely used for assessing brain atrophy, which is a key indicator for the onset and progression of many neuro-degenerative diseases. Image analysis techniques help quantify brain atrophy by classifying the brain tissue voxels into different tissue classes such as Gray Matter (GM), White Matter (WM), and Cerobrospinal Fluid (CSF). Brain tissue classification is particularly useful in assessing brain atrophy, since the gray matter volume serves as a biomarker for cortical atrophy.

However, automated tissue classification techniques sometimes provide erroneous tissue classification maps, due to various reasons such as:
i. Remaining bias-field (even after bias-field correction)
ii. Noise
iii. Motion artifacts
iv. Low spatial resolution due to low magnetic field strength
v. Lesions
As a result, typically two types of tissue classification errors may occur in the tissue classification map, namely isolated "blob-like" misclassifications, as well as over- or under-pronunciation of cortical gray matter near its border to white matter.
Disadvantageous, such areas of misclassification in a tissue classification map may hinder the further detection and differential diagnosis of neuro-degenerative diseases.

US 2002/0186882 A1 discloses a process and related apparatus for obtaining quantitative data about a 2-dimensional, 3-dimensional image, or other dimensional image, e.g. for classifying and counting the number of entities an image contains. Each entity comprises an entity, structure, or some other type of identifiable portion of the image having definable characteristics. The entities located within an image may have a different shape, color, texture, or other definable characteristic, but still belong to the same classification. In other instances, entities comprising a similar color, and texture may be classified as one type while entities comprising a different color, and texture may be classified as another type. An image may contain multiple entities and each entity may belong to a different class. Thus, the system may quantify image data according to a set of changing criteria and derive one or more classifications for the entities in the image. Once the image data is classified, the total number of entities in the image is calculated and presented to the user. Embodiments provide a way for a computer to determine what kind of entities (e.g., entities) are in an image and counts the total number of entities that can be visually identified in the image. Information utilized during a training process may be stored and applied across different images.

SUMMARY OF THE INVENTION

It would be advantageous to have a system or method for brain tissue classification which enables areas of misclassification to be corrected.

The following aspects of the invention involve a user interactively providing user feedback on an area of misclassification in the tissue classification map, with the user feedback further being indicative of a correction of the misclassification. Rather than directly correcting the tissue classification map based on the user feedback, the user feedback is used to adjust a prior probability map which is used as input in the automated tissue classification technique, thereby obtaining an adjusted prior probability map. The automated tissue classification technique is then re-run based on the adjusted prior probability map.

A first aspect of the invention provides a system for brain tissue classification, the system comprising:
   an image data interface for accessing an image of a brain of a patient;
   a processor configured to apply an automated tissue classification technique to the image based on a prior probability map, the prior probability map being registered to the image and being indicative of a probability of a particular location in the brain belonging to a particular brain tissue class, the automated tissue classification technique providing as output a tissue classification map of the brain of the patient;
   a user interaction subsystem comprising:
   i) a display output for displaying the tissue classification map on a display,
   ii) a user device input for receiving input commands from a user device operable by a user, wherein the input commands represent user feedback which is indicative of a) an area of misclassification in the tissue classification map and b) a correction of the misclassification;
   wherein the processor is configured to:
   j) adjust the prior probability map based on the user feedback, thereby obtaining an adjusted prior probability map, and
   jj) re-apply the automated tissue classification technique to the image based on the adjusted prior probability map.

A further aspect of the invention provides a workstation or imaging apparatus comprising the system.

A further aspect of the invention provides a method for brain tissue classification, the method comprising:
   accessing an image of a brain of a patient;
   applying an automated tissue classification technique to the image based on a prior probability map, the prior probability map being registered to the image and being indicative of a probability of a particular location in the brain belonging to a particular brain tissue class, the automated tissue classification technique providing as output a tissue classification map of the brain of the patient;

displaying the tissue classification map on a display;

receiving input commands from a user device operable by a user, wherein the input commands represent user feedback which is indicative of a) an area of misclassification in the tissue classification map and b) a correction of the misclassification;

adjusting the prior probability map based on the user feedback, thereby obtaining an adjusted prior probability map; and re-applying the automated tissue classification technique to the image based on the adjusted prior probability map.

A further aspect of the invention provides a computer program product comprising instructions for causing a processor system to perform the method.

The above measures involve accessing an image of a brain of a patient. The image may thus represent a brain scan, and may be obtained from various imaging modalities, including but not limited to T1-weighted Magnetic Resonance Imaging (MRI). An automated tissue classification technique is applied to the image based on a prior probability map. Such prior probability maps are known per se, and may describe the likelihood of a known position in the brain belonging to one of the various tissue classes. Typically, these prior probability maps have been generated from a sample cohort of correctly classified brain scans.

Automated tissue classification techniques which use prior probability maps are also known per se, e.g., from the field of medical image analysis. The prior probability map is registered with the image, e.g., in a manner known per se from the field of medical image registration. As a result of the automated tissue classification, a tissue classification map is obtained, locally classifying the brain according to brain tissue type.

It is noted that here and in the following, the term 'brain tissue classification' is used interchangeably with 'brain tissue segmentation' as the resulting tissue classification map segments the brain into the various tissue types and thereby provides a segmentation.

Having obtained the tissue classification map, the tissue classification map is displayed on a display and a user is enabled to provide user feedback which is indicative of an area of misclassification in the tissue classification map and which is indicative of a correction of the misclassification. As such, the user provides user feedback which is indicative of where a misclassification occurred and at what the correction should be. For example, the user feedback may indicate a region to be biased towards white matter.

The prior probability map is then adjusted based on the user feedback, yielding an adjusted prior probability map which comprises one or more local corrections of probabilities. The automated tissue classification technique is then re-run based on the adjusted prior probability map, yielding a further tissue classification map.

The above measures have as effect that a user is enabled to provide user feedback which is indicative of where a misclassification occurred and what the correction should be. Rather than directly correcting the tissue classification map based on the user feedback, the user feedback is used to adjust the prior probability map, and the automated tissue classification technique is then re-run based on the adjusted prior probability map.

The inventors have recognized that in case of an automated tissue classification technique providing an erroneous tissue classification map, it may, counterintuitively, be preferred to adjust an input of the automated tissue classification technique, namely the prior probability map, rather than to directly correct its output, namely the tissue classification map. A reason for that is that user feedback may not be accurate enough to directly correct the tissue classification map. Namely, such direct correction may require, e.g., an accurate delineation of the area of misclassification, an accurate indication of the brain tissue type, etc. Such accurate user feedback may not be available or may impose an unduly high burden on the user. As such, the inventors devised to adjust the prior probability map and re-run the automated tissue classification technique on the entire image using the adjusted prior probability map. This provides a degree of indirection, in that the user feedback is used to adjust probabilities rather than the classification directly.

Advantageously, it is not needed for the user to indicate the area of misclassification and/or the correction of the misclassification with a highest degree of accuracy. Rather, it may suffice to provide an approximate indication thereof. Conversely, given user feedback of a certain degree of accuracy, a more accurate tissue classification map may be obtained compared to a direct correction of the tissue classification map. Another advantage is that tissue classification elsewhere in the brain may also improve, since the contrast between tissue classes can be better modelled by having more 'supervised' evidence.

Optionally,
the user interaction subsystem is configured to enable the user to indicate a point in the area of misclassification, thereby obtaining a user-indicated point;
the processor is configured to determine a boundary of the area of misclassification based on the user-indicated point.

The user may thus suffice with indicating a point which lies within the area of the misclassification. Such a user-indicated point may nevertheless enable the system to determine the (entire) area of the misclassification, namely by making use of a boundary detection technique. For example, the processor may consider the user-indicated point as a seed point in a region-growing technique, thereby obtaining the boundary of the area of misclassification. Alternatively, other boundary detection techniques may be used, as known per se from the field of medical image analysis, including but not limited to connected component analysis and techniques based on morphological operations.

Optionally, the user interaction subsystem is configured to enable the user to indicate the correction of the misclassification by manually specifying a brain tissue class, thereby obtaining a user-specified brain tissue class. It may occur that the user is able to directly determine the brain tissue class in the area of misclassification. The user is enabled to provide such user feedback, namely by directly specifying the brain tissue class.

Optionally, the processor is configured to adjust the prior probability map by increasing, in the prior probability map, a probability of the user-specified brain tissue class in the area of misclassification. Based on the user directly specifying the brain tissue class, the probability of said brain tissue class may be increased in the prior probability map within the area of misclassification. For example, the probability may be increased to 80% or higher, 90% or higher, 95% or higher, or to substantially 100%, e.g., to 99% or higher.

Optionally, the user interface subsystem is configured to enable the user to indicate the correction of the misclassification by changing a probability ratio between grey matter tissue and white matter tissue. The changing of the probability ratio between grey matter tissue and white matter tissue has been found to be a particularly advantageous way of providing user feedback in case of over- or under-pronunciation of cortical gray matter near its border to white matter. For example, the user may be enabled to incrementally change the probability ratio, e.g., by dragging a mouse up or down while pressing the left mouse button, by operating specific keys on a keyboard (e.g., the plus and minus keys), etc.

Optionally, the user interaction subsystem is configured to enable the user to indicate the area of misclassification in the tissue classification map as displayed on the display. The user is thus enabled to specifically indicate the area of misclassification, as it occurs in the tissue classification map, in the tissue classification map itself. For example, the user may use an annotation tool to draw a contour in the displayed tissue classification map.

Optionally, the user interface subsystem is configured to:
  display the image on the display, and
  enable the user to indicate the area of misclassification in the tissue classification map by indicating a region of interest in the image.

As an alternatively to indicating the area of misclassification, as it occurs in the tissue classification map, in the tissue classification map itself, the user may indicate said area in the image, which may be displayed simultaneously with the tissue classification map. For example, the user may use an annotation tool to draw a contour in the displayed image.

Optionally, the automated tissue classification technique is based on Expectation Maximization. Automated tissue classification techniques based on Expectation Maximization, in combination with Markov Random Fields regularization, have recently shown to give a best overall performance in academic literature. However, other automated tissue classification techniques which use prior probability maps may be used as well.

It will be appreciated by those skilled in the art that two or more of the above-mentioned embodiments, implementations, and/or optional aspects of the invention may be combined in any way deemed useful.

Modifications and variations of the imaging apparatus, the workstation, the method, and/or the computer program product, which correspond to the described modifications and variations of the system, can be carried out by a person skilled in the art on the basis of the present description.

A person skilled in the art will appreciate that the method may be applied to multi-dimensional image data, e.g. to two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the Figures, elements which correspond to elements already described may have the same reference numerals.

LIST OF REFERENCE NUMBERS

Figure 1:
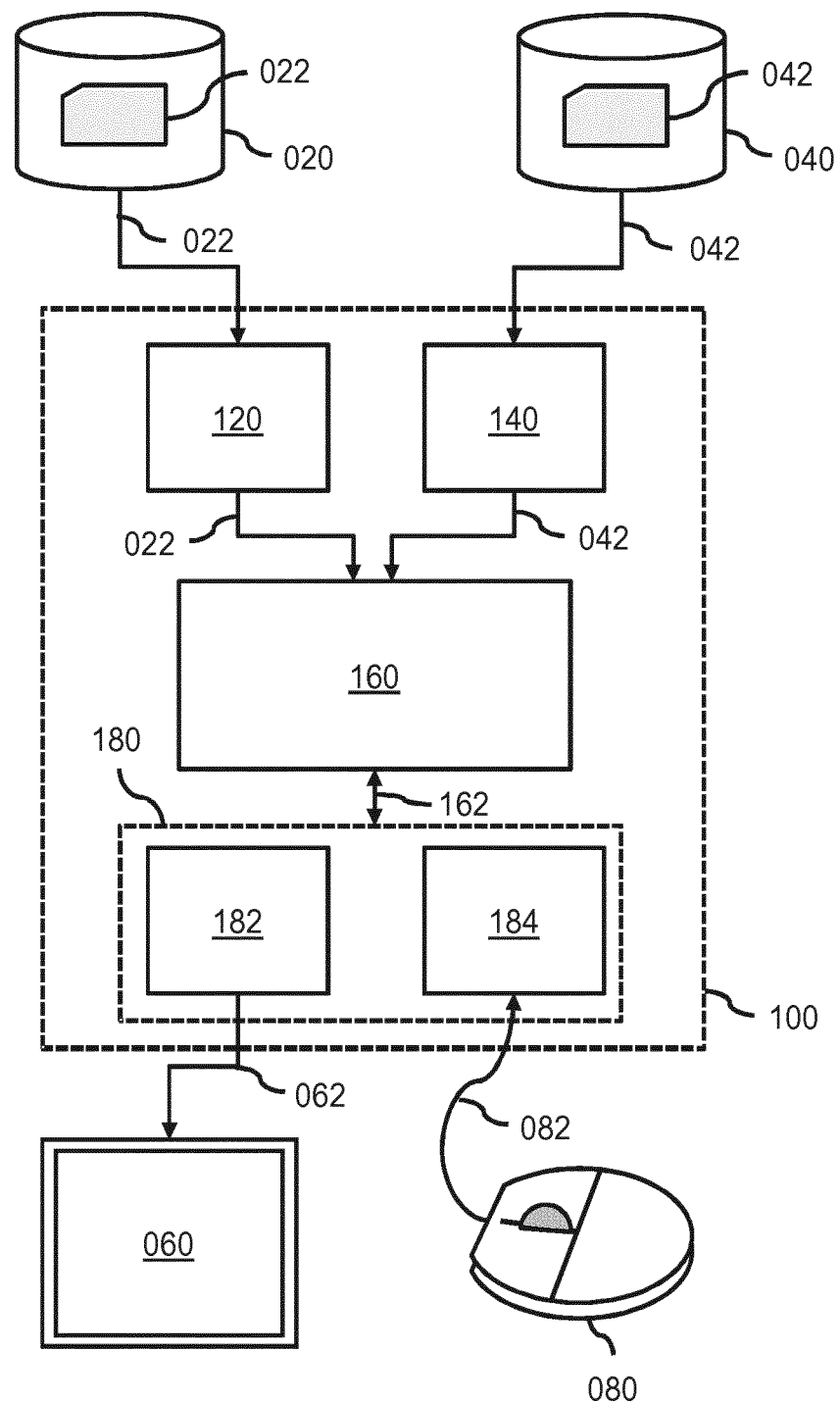
FIG. 1 shows a system for brain tissue classification, in which a prior probability map is adjusted based on user feedback and the adjusted prior probability map is used to re-apply an automated tissue classification technique to a brain image.

The following list of reference numbers is provided for facilitating the interpretation of the drawings and shall not be construed as limiting the claims.

020 image repository
022 image data of medical image
024, 026 medical image
030, 032, 034A, 034B tissue classification map
036, 038 indication of classification error
040 database
042 data representing prior probability map
060 display
062 display data
064 onscreen cursor
070 user-indicated point
072 segmentation
080 user device
082 input commands
100 system for brain tissue classification
120 image data interface
140 prior probability data interface
160 processor
162 communication to/from user interaction subsystem
180 user interaction subsystem
182 display output
184 user device input
200 method for brain tissue classification
210 accessing brain image
220 applying automated tissue classification 230 displaying tissue classification map
240 receiving user feedback
250 adjusting prior probability map
260 re-applying automated tissue classification
270 computer readable medium
280 instructions stored as non-transient data

DETAILED DESCRIPTION OF EMBODIMENTS

FIG. 1 shows a system 100 for brain tissue classification. Such a system may be used in various medical applications, including, but not limited to, the detection and differential diagnosis of neuro-degenerative diseases. During operation, the system 100 may, briefly stated, apply an automated tissue classification technique to an image of a brain based on a prior probability map, thereby obtaining a tissue classification map of the brain. A user is then enabled to, using a user interaction subsystem, provide user feedback which is indicative of a) an area of misclassification in the tissue classification map and b) a correction of the misclassification. The system may then adjust the prior probability map based on the user feedback to obtain an adjusted prior probability map, and re-apply the automated tissue classification technique to the image based on the adjusted prior probability map.

The system 100 comprises an image data interface 120 for accessing an image 022 of a brain of a patient, henceforth also referred to simply as brain image 022. In the example of FIG. 1, the image data interface 120 is shown to be connected to an external image repository 020 which comprises the brain image 022. For example, the image repository 020 may be constituted or be part of a Picture Archiving and Communication System (PACS) of a Hospital Information System (HIS) to which the system 100 may be connected or comprised in. Accordingly, the system 100 may obtain access to the brain image 022. Alternatively, the brain image 022 may be accessed from an internal data storage of the system 100. In general, the image data interface 120 may take various forms, such as a network interface to a local or wide area network, e.g., the Internet, a storage interface to an internal or external data storage, etc. It is further noted that, where applicable, a reference to the brain image 022 is to be understood as a reference to the image's image data.

The system 100 further comprises a processor 160 configured to apply an automated tissue classification technique to the brain image 022 based on a prior probability map 042. For that purpose, the processor 160 is shown to receive the brain image 022 from the image data interface 120, and the prior probability map 040 from a prior probability data interface 140. Said prior probability data interface 140 may enable the system 100 to access the prior probability map 042 on an external database 040, such as a PACS. Alternatively, the system 100 may access the prior probability map 042 internally or from another source. As in the case of the image data interface 120, the prior probability data interface 140 may take various forms, including but not limited to a network interface to a local or wide area network, e.g., the Internet, a storage interface to an internal or external data storage, etc. As output, a tissue classification map 162 of the brain of the patient is then obtained.

The system 100 further comprises a display output 182 for displaying visual output of the system 100 on a display 060, with the visual output including at least the tissue classification map. For displaying the tissue classification map, the display output 182 is shown to internally communicate with the processor 162, e.g., to obtain data visualizing the tissue classification map, and to provide display data 062 to the display 060.

The system 100 further comprises a user device input 184 for receiving input commands 082 from a user device 080 operable by a user. The user device 080 may take various forms, including but not limited to a computer mouse 080, touch screen, keyboard, etc. The user device input 184 may be of a type which corresponds to the type of user device 080. Together, the display output 182 and the user device input 184 may form a user interaction subsystem 180 which enables the user to interactively provide user feedback to the system 100. In particular, the user feedback may be indicative of a) an area of misclassification in the tissue classification map and b) a correction of the misclassification. As a non-limiting example, the user may click on a part of the tissue classification map which is incorrectly classified and select a correct classification from an on-screen menu. The user feedback may then be available to the system 100 in the form of user feedback data indicating, for example, coordinate(s) of the misclassification in a coordinate system associated with the tissue classification map, and data indicative of the correction.

Having obtained the user feedback from the user device input 184, the processor 160 may adjust the prior probability map based on the user feedback, thereby obtaining an adjusted prior probability map, and subsequently re-apply the automated tissue classification technique to the image based on the adjusted prior probability map.

It is noted that various operations of the system 100, including various optional aspects thereof, will be explained in more detail with reference to FIGS. 2-4C.

The system 100 may be embodied as, or in, a single device or apparatus, such as a workstation or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model.

Figure 2A:
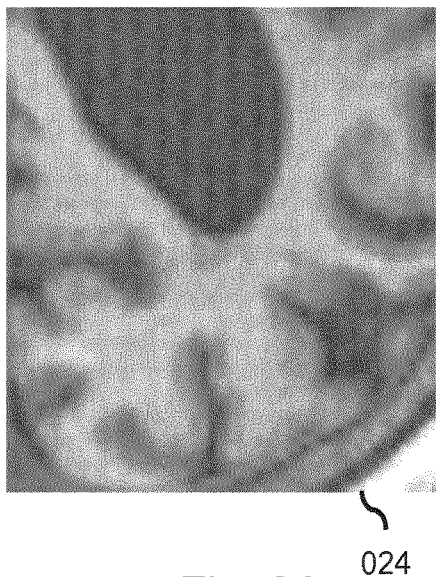
FIG. 2A shows a part of a MRI image.
Figure 2B:
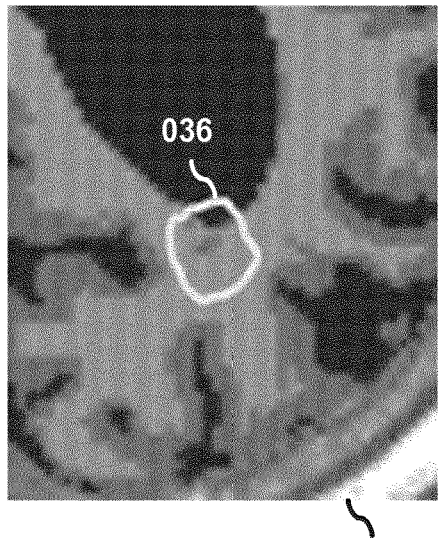
FIG. 2B shows a tissue classification map obtained from an automated tissue classification of the MRI image, with the tissue classification map containing a misclassification in the form of a blob-like region having been incorrectly classified as cortical gray matter rather than white matter.
Figure 3A:
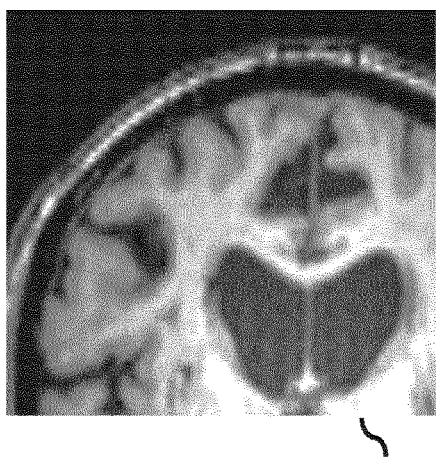
FIG. 3A shows a part of another MRI image.
Figure 3B:
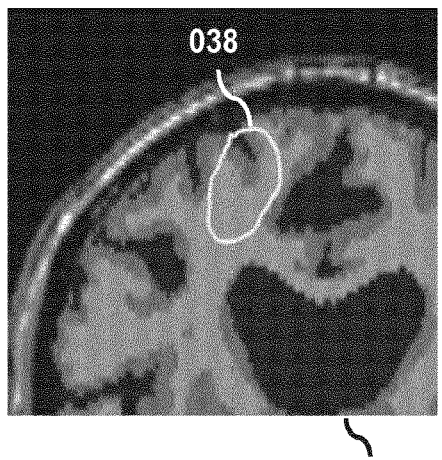
FIG. 3B shows a tissue classification map obtained from an automated tissue classification of the MRI image, with the tissue classification map containing a misclassification in the form of cortical gray matter being under-pronounced at the border to white matter.

FIGS. 2A-3B illustrate two common types of tissue classification errors, namely isolated "blob-like" misclassifications (FIGS. 2A-2B), as well as over- or under-pronunciation of cortical gray matter near its border to white matter (FIGS. 3A-3B).

FIG. 2A shows part of a MRI image 024, and FIG. 2B shows a tissue classification map 030 obtained from an automated tissue classification of the MRI image. In FIG. 2B, blue (black in a greyscale reproduction) indicates Cerebro-Spinal Fluid (CSF), green (dark gray in a greyscale reproduction) indicates Gray Matter (GM), and pink (light grey in a greyscale reproduction) indicates White matter (WM). As indicated in FIG. 2B by a marking 036, the tissue classification map 030 contains a misclassification in the form of a blob-like region having been incorrectly classified as cortical gray matter rather than white matter.

FIG. 3A shows a part of another MRI image 026, and FIG. 3B shows a tissue classification map 032 obtained from an automated tissue classification of the MRI image. A same color (or greyscale) coding is applied as in FIG. 2B. As indicated in FIG. 3B by a marking 038, the tissue classification map 032 of FIG. 3B contains a misclassification in the form of cortical gray matter being under-pronounced at the border to white matter.

The above classification errors may frequently occur, e.g., for the reasons indicated in the background section, thereby yielding erroneous tissue classification maps.

As introduced with reference to FIG. 1, the user may provide user feedback to the system which is indicative of a) an area of misclassification in the tissue classification map and b) a correction of the misclassification. Such user feedback may take various forms.

Figure 4A:
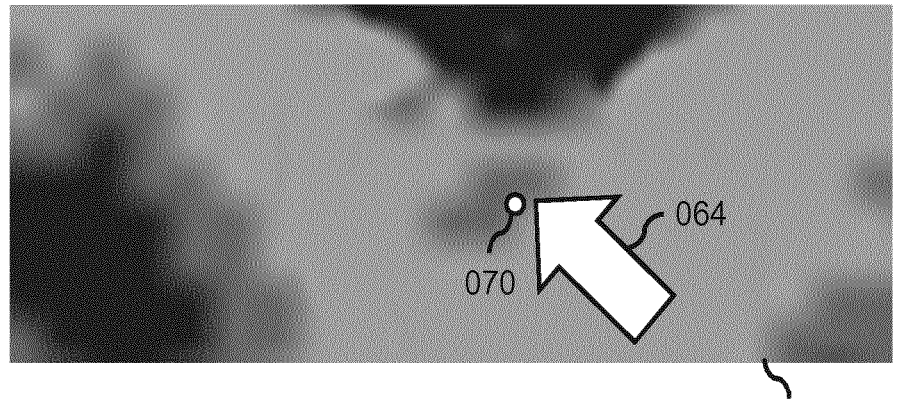
FIG. 4A illustrate the user providing user feedback which is indicative of the area of misclassification by indicating a point in the area of misclassification.
Figure 4B:
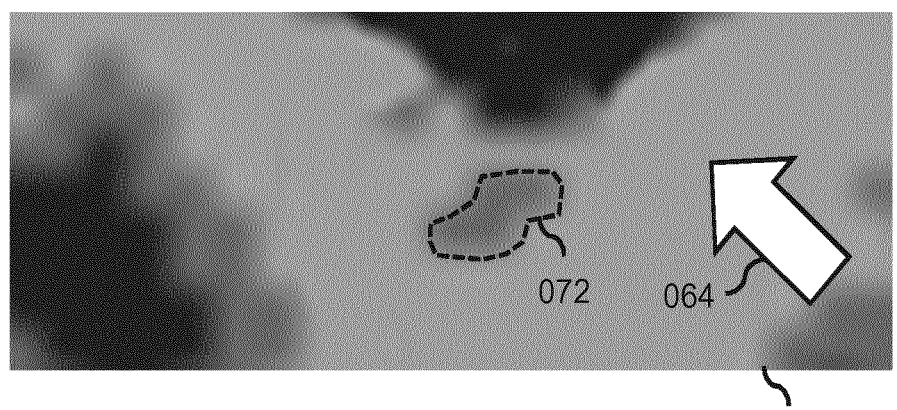
FIG. 4B shows a result of a boundary of the area of misclassification being automatically determined based on the user-indicated point.

FIG. 4A illustrates a particular example of such user feedback, namely the user indicating a point 070 in the area of misclassification. The example is based on the blob-like misclassification show in FIG. 2B, with FIGS. 4A-4B showing a zoomed-in part of the corresponding tissue classification map 034A. The user may indicate the point 070 in various ways. For example, the user may click on a position in the displayed tissue classification map 034A with an on-screen cursor 064. As a result of the user indicating the point 070 in the area of misclassification, a boundary of the area of misclassification may then be determined, e.g., using a boundary detection technique. For example, the user-indicated point 070 may be considered as a seed point in a region-growing technique, thereby obtaining the boundary of the area of misclassification. Alternatively, other boundary detection techniques may be used, as known per se from the field of medical image analysis, including but not limited to connected component analysis and techniques based on morphological operations. The resulting boundary 072 is indicated in FIG. 4B as a dashed-line delineating the blob-like misclassification in the tissue classification map 034A from its surroundings.

Figure 4C:
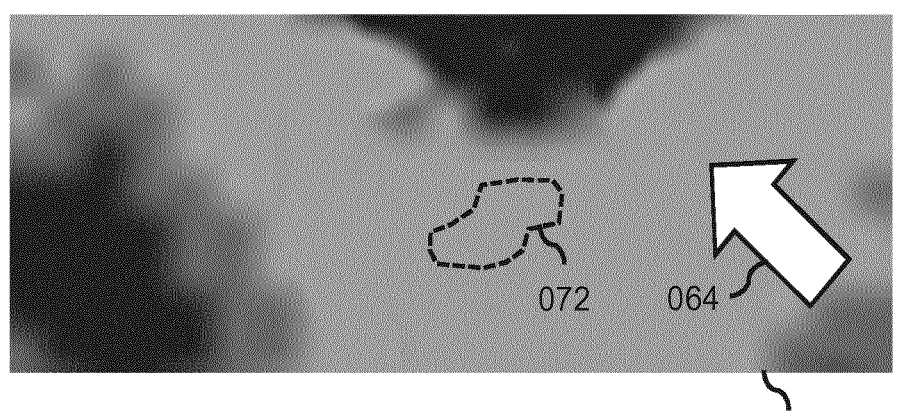
FIG. 4C illustrates a result of the user indicating the correction of the misclassification by manually specifying a brain tissue class.

FIG. 4C illustrates a result of the user further indicating the correction of the misclassification. Namely, the user may manually specify a brain tissue class which is to be applied to the misclassified area 072. As a non-limiting example, the user may select a correct brain tissue class from an on-screen menu (menu not shown in FIG. 4C). The correction may be shown to the user, namely by the misclassified area 072 being corrected in the displayed tissue classification map 034A to the user-specified brain tissue class. As shown in FIG. 4C, the area may be classified as white matter rather than grey matter.

Having provided the user feedback on a) the area of misclassification in the tissue classification map and b) the correction of the misclassification, the prior probability map may then be adjusted, thereby obtaining an adjusted prior probability map. It is noted that the original and adjusted prior probability maps are not explicitly shown in view of such probability maps being difficult to adequately visualize by way of each location in the map typically having probability values for each brain tissue class, thereby hindering a greyscale or even color-based visualization. However, conceptually, the adjustment may take a similar form as that shown for the tissue classification map 034A, 034B in FIG. 4B and FIG. 4C, in that a corresponding region in the prior probability map may be adjusted by increasing the probability of the user-specified brain tissue class in the area of misclassification to substantially 100%, effectively 'overwriting' existing probability values. Having adjusted the prior probability map, the automated tissue classification technique may then be re-applied to the image, yielding a different, typically (much) improved tissue classification map.

In general, besides indicating a point, other options may exist for the user to indicate the area of misclassification in the tissue classification map. For example, the user may directly delineate the misclassified area in the tissue classification map. Another example is that the user may indicate a point in the misclassified area, with the system then assuming the misclassified area to be a predetermined area around the point.

It is also noted that the misclassified area, which exists in the tissue classification map, may not be indicated by the user in the tissue classification map but rather elsewhere. For example, the user may learn the area of misclassification from studying the displayed tissue classification map, but may then indicate said area to the system in the image itself, e.g., by drawing a rectangle and thereby marking a region in the image.

There also exist various options for the user to indicate the correction of the misclassification. A first example is the aforementioned direct specifying of the correct brain tissue class. Another example is that a user may rather change a probability ratio between brain tissue classes, such as the probability ratio between grey matter tissue and white matter tissue. As such, the correction is not a binary correction in class but rather a correction in probability. Such probability ratio may be changed incrementally, e.g., in steps. The system may or may not re-apply the automated tissue classification technique to the image after each incremental change. Yet another example is that the system may automatically propagate the probabilities surrounding the misclassified area into the misclassified area. As such, the indication of the misclassified area thereby effectively also serves for indicating the correction of the misclassification, in that it is assumed to follow from its surroundings.

In accordance with the above, an example use-case may be the following. Here, a user may point and click to a location in a blob-like misclassified region and assign a correct label to the region, e.g., via a drop-down box. This activity may trigger the following operations: 1) the boundary of the misclassified region may be automatically determined based on a local analysis of voxels in the labeled image, e.g., by connected component analysis, morphological operations, or region growing using the labels of the segmented image, 2) assignment of a fixed label to voxels in the region in the form of a 100% probability of voxels in the region belonging to the chosen tissue class, and 3) automatic optimization of the global tissue classification result by re-running the automated tissue classification algorithm, but now using the prior probability map with local modifications.

Another example use-case may be the following. Here, the user may mark a region of interest and continuously change its probability of belonging to a particular brain tissue class in an interactive way. Once satisfied, the automated tissue classification algorithm may be re-run. This use-case may involve the following operations:

1) The user may mark the region of interest with an image contouring tool. For example, the user may draw a contour or use an annotation tool with a specific shape, such as a disk or a rectangle. Since the brain scan may be a 3D scan and the user may be shown a 2D image slice of the 3D scan, the region may be automatically extended/propagated to 2D image slices before and behind the displayed image slice with known techniques, such as a 3D annotation tool with a spherical shape instead of a disk.
2) Once the region of interest is marked, the user may start an interactive operation that increases/decreases prior probability values for gray matter as opposed to white matter. The changes in probability value may be indicated using, e.g., specific keys on the keyboard (+/−), by pressing the left mouse button and moving the mouse up/down, etc.

3) Re-running the automated tissue classification algorithm, but now using the prior probability map with local modifications.

It will be appreciated that a number of approaches exist for automated tissue classification. Algorithms based on Expectation Maximization (EM) and Markov Random Fields regularization have, at the time of invention, shown to give best overall performance (see http://mrbrains13.isi.uu.nl/results.php for results and corresponding papers). However, other automated tissue classification techniques which use prior probability maps may be used as well. With further reference to EM-based approaches: the expectation maximization utilizes prior probability maps, which describe the likelihood of a known position in the brain belonging to one of the possible brain tissue classes. Typically, these prior probability maps have been generated from a sample cohort of correctly segmented brain scans, which are spatially aligned, i.e., registered. For a new subject, prior probability maps may be registered to the brain scan in a pre-processing step. Then, the expectation maximization algorithm may iteratively perform two steps: (i) a so-termed M-Step, in which, given the tissue class probabilities for each voxel, an intensity model may be determined/updated for a specific brain tissue class, and (ii) a so-termed E-Step, in which, given the (updated) intensity model for a specific brain tissue class, the voxel-wise probabilities may be refined.

It is further noted that it may not be needed or desired to adjust the probability map. Rather, a parameter or configuration of the automated tissue classification technique may be adjusted. A specific example is that the misclassified area may have been corrected by the user, e.g., in an interactive manner as indicated with reference to FIGS. 4A-4C. The automated tissue classification technique may then be re-run on a region of interest that does not include the user-identified misclassified area. For example, the user-identified misclassified area may be excluded from a binary voxel mask that defines the region of interest. The final tissue classification map may then be composed of the results from the automated tissue classification technique in the region of interest, together with the misclassified area as interactively corrected by the user. It will be appreciated that, in addition to the abovementioned example of excluding the manually corrected area from a region of interest, other adjustments of parameters or configurations of the automated tissue classification technique are within reach of the skilled person.

Figure 5:
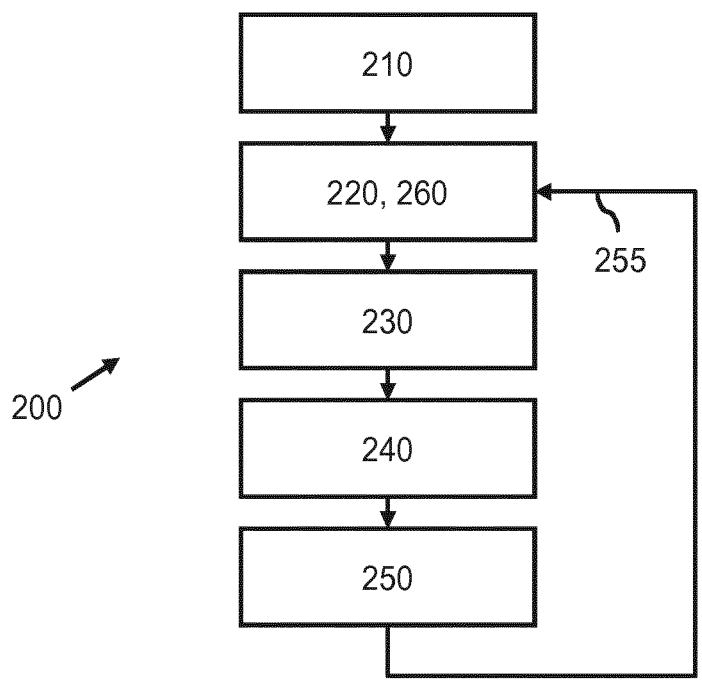
FIG. 5 shows a method for brain tissue classification, in which a prior probability map is adjusted based on user feedback and the adjusted prior probability map is used to re-apply an automated tissue classification technique to a brain image.

FIG. 5 shows a method 200 for brain tissue classification. The method 200 comprises, in an operation titled "ACCESSING BRAIN IMAGE", accessing 210 an image of a brain of a patient. The method 200 further comprises, in an operation titled "APPLYING AUTOMATED TISSUE CLASSIFICATION", applying 220 an automated tissue classification technique to the image based on a prior probability map, the prior probability map being registered to the image and being indicative of a probability of a particular location in the brain belonging to a particular brain tissue class, the automated tissue classification technique providing as output a tissue classification map of the brain of the patient. The method 200 further comprises, in an operation titled "DISPLAYING TISSUE CLASSIFICATION MAP", displaying 230 the tissue classification map on a display. The method 200 further comprises, in an operation titled "RECEIVING USER FEEDBACK", receiving 240 input commands from a user device operable by a user, wherein the input commands represent user feedback which is indicative of i) an area of misclassification in the tissue classification map and ii) a correction of the misclassification. The method 200 further comprises, in an operation titled "adjusting prior probability map", adjusting 250 the prior probability map based on the user feedback, thereby obtaining an adjusted prior probability map. The method 200 further comprises, in an operation titled "RE-APPLYING AUTOMATED TISSUE CLASSIFICATION", re-applying 260 the automated tissue classification technique to the image based on the adjusted prior probability map.

It will be appreciated that the above operation may be performed in any suitable order, e.g., consecutively, simultaneously, or a combination thereof, subject to, where applicable, a particular order being necessitated, e.g., by input/output relations.

As a non-limiting example, FIG. 5 shows the method 200 being performed in an iterative manner, namely by the operations of applying 220 and re-applying 260 being indicated as being essentially a similar step by way of the arrow 255, albeit being performed at a later stage and using different input, namely different prior probability maps.

Figure 6:
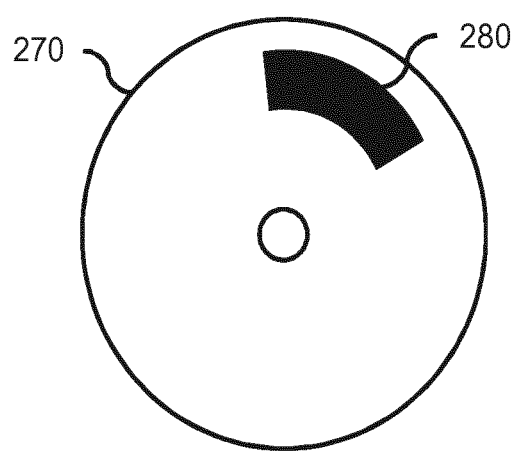
FIG. 6 shows a computer readable medium comprising instructions for causing a processor system to perform the method.

The method 200 may be implemented on a computer as a computer implemented method, as dedicated hardware, or as a combination of both. As also illustrated in FIG. 6, instructions for the computer, e.g., executable code, may be stored on a computer readable medium 270, e.g., in the form of a series 280 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 6 shows an optical disc 270.

It will be appreciated that although the invention as claimed as been described with reference to brain tissue classification, the invention as claimed may equally be applied to another type of classification which uses prior probability maps as input.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for brain tissue classification, comprising:
   an image data interface for accessing an image of a brain of a patient;
   a processor configured to apply an automated tissue classification technique to the image based on a prior probability map, the prior probability map being registered to the image and being indicative of a probability of a particular location in the brain belonging to a particular brain tissue class, the automated tissue classification technique providing as output a tissue classification map of the brain of the patient;
   a user interaction subsystem configured to enable the user to indicate a point in the area of misclassification, thereby obtaining a user-indicated point, comprising:
   i) a display output for displaying the tissue classification map on a display,
   ii) a user device input for receiving input commands from a user device operable by a user, wherein the input commands represent user feedback which is indicative of a) an area of misclassification in the tissue classification map and b) a correction of the misclassification, the user feedback indicating a point in the area of misclassification, thereby obtaining a user-indicated point; wherein the processor is configured to:
   determine a boundary of the area of misclassification based on the user-indicated point,
   adjust the prior probability map based on the user feedback, thereby obtaining an adjusted prior probability map, and
   re-apply the automated tissue classification technique to the image based on the adjusted prior probability map.

2. The system according to claim 1, wherein the user interaction subsystem is configured to enable the user to indicate the correction of the misclassification by manually specifying a brain tissue class, thereby obtaining a user-specified brain tissue class.

3. The system according to claim 2, wherein the processor is configured to adjust the prior probability map by increasing, in the prior probability map, a probability of the user-specified brain tissue class in the area of misclassification.

4. The system according to claim 3, wherein the processor is configured to increase, in the prior probability map, the probability of the user-specified brain tissue class in the area of misclassification to substantially 100%.

5. The system according to claim 1, wherein the user interface subsystem is configured to enable the user to indicate the correction of the misclassification by changing a probability ratio between grey matter tissue and white matter tissue.

6. The system according to claim 5, wherein the user interface subsystem is configured to enable the user to incrementally change the probability ratio.

7. The system according to claim 1, wherein the user interaction subsystem configured to enable the user to indicate the area of misclassification in the tissue classification map as displayed on the display.

8. The system according to claim 1, wherein the user interface subsystem is configured to:
   display the image on the display, and
   enable the user to indicate the area of misclassification in the tissue classification map by indicating a region of interest in the image.

9. The system according to claim 1, wherein the automated tissue classification technique is based on Expectation Maximization.

10. Workstation comprising the system according to claim 1.

11. Imaging apparatus comprising the system according to claim 1.

12. Method for brain tissue classification, comprising:
    accessing an image of a brain of a patient;
    applying an automated tissue classification technique to the image based on a prior probability map, the prior probability map being registered to the image and being indicative of a probability of a particular location in the brain belonging to a particular brain tissue class, the automated tissue classification technique providing as output a tissue classification map of the brain of the patient;
    enabling a user to indicate a point in the area of misclassification, thereby obtaining a user-indicated point;
    displaying the tissue classification map on a display;
    receiving input commands from a user device operable by the user, wherein the input commands represent user feedback which is indicative of i) an area of misclassification in the tissue classification map and ii) a correction of the misclassification; the user feedback indicating a point in the area of misclassification, thereby obtaining a user-indicated point;

determining a boundary of the area of misclassification based on the user-indicated point;

adjusting the prior probability map based on the user feedback, thereby obtaining an adjusted prior probability map; and re-applying the automated tissue classification technique to the image based on the adjusted prior probability map.

13. A non-transitory computer readable medium comprising instructions for causing a processor to perform a method comprising the steps of:

accessing an image of a brain of a patient;

applying an automated tissue classification technique to the image based on a prior probability map, the prior probability map being registered to the image and being indicative of a probability of a particular location in the brain belonging to a particular brain tissue class, the automated tissue classification technique providing as output a tissue classification map of the brain of the patient;

displaying the tissue classification map on a display;

receiving input commands from a user device operable by the user, wherein the input commands represent user feedback which is indicative of i) an area of misclassification in the tissue classification map and ii) a correction of the misclassification; the user feedback indicating a point in the area of misclassification, thereby obtaining a user-indicated point;

determining a boundary of the area of misclassification based on the user-indicated point;

adjusting the prior probability map based on the user feedback, thereby obtaining an adjusted prior probability map; and re-applying the automated tissue classification technique to the image based on the adjusted prior probability map.

* * * * *